(12) United States Patent
Higgins et al.

(10) Patent No.: US 10,595,895 B2
(45) Date of Patent: Mar. 24, 2020

(54) ROTATIONAL MEDICAL DEVICE WITH AIRFOIL

(71) Applicant: CARDIOVASCULAR SYSTEMS, INC., St. Paul, MN (US)

(72) Inventors: Joseph P. Higgins, Minnetonka, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 118 days.

(21) Appl. No.: 15/651,327

(22) Filed: Jul. 17, 2017

(65) Prior Publication Data
US 2018/0125527 A1 May 10, 2018

Related U.S. Application Data

(60) Provisional application No. 62/364,037, filed on Jul. 19, 2016.

(51) Int. Cl.
*A61B 17/3207* (2006.01)
*A61B 17/32* (2006.01)

(52) U.S. Cl.
CPC ........ *A61B 17/320758* (2013.01); *A61B 2017/320004* (2013.01); *A61B 2017/320766* (2013.01)

(58) Field of Classification Search
CPC ........ A61B 17/3207; A61B 17/320758; A61B 2017/32004; A61B 2017/320766; A61B 17/32; A61B 17/22; A61B 17/320725
See application file for complete search history.

(56) References Cited

U.S. PATENT DOCUMENTS

| | | |
|---|---|---|
| 5,030,201 A | 7/1991 | Palestrant |
| 5,681,336 A | 10/1997 | Clement et al. |
| 2002/0007190 A1 | 1/2002 | Wulfman et al. |
| 2002/0077638 A1 | 6/2002 | Kadavy et al. |
| 2002/0147458 A1 | 10/2002 | Hiblar et al. |
| 2003/0125756 A1 | 7/2003 | Shturman et al. |
| 2004/0006358 A1 | 1/2004 | Wulfman et al. |
| 2008/0306498 A1 | 12/2008 | Thatcher et al. |
| 2009/0171448 A1 | 7/2009 | Eli |
| 2012/0316634 A1 | 12/2012 | Shalev et al. |

FOREIGN PATENT DOCUMENTS

| | | |
|---|---|---|
| EP | 1923008 A1 | 5/2008 |
| WO | 2009/065927 | 5/2009 |

OTHER PUBLICATIONS

International Search Report and Written Opinion, dated Oct. 6, 2017 for PCT Application No. PCT/US17/42505, filed Jul. 18, 2017.
Extended European Search Report issued in related application, dated Oct. 31, 2019.

*Primary Examiner* — George J Ulsh
(74) *Attorney, Agent, or Firm* — Barnes & Thornburg LLP; Jeffrey R. Stone

(57) ABSTRACT

A rotational medical device comprising an airfoil on a rotational drive shaft to generate lift forces generally directed radially away from a rotational axis of the drive shaft, thereby enabling the drive shaft and/or a working element thereon to achieve a working diameter during rotation that is greater than the resting diameter of the drive shaft and/or a working element thereon.

8 Claims, 7 Drawing Sheets

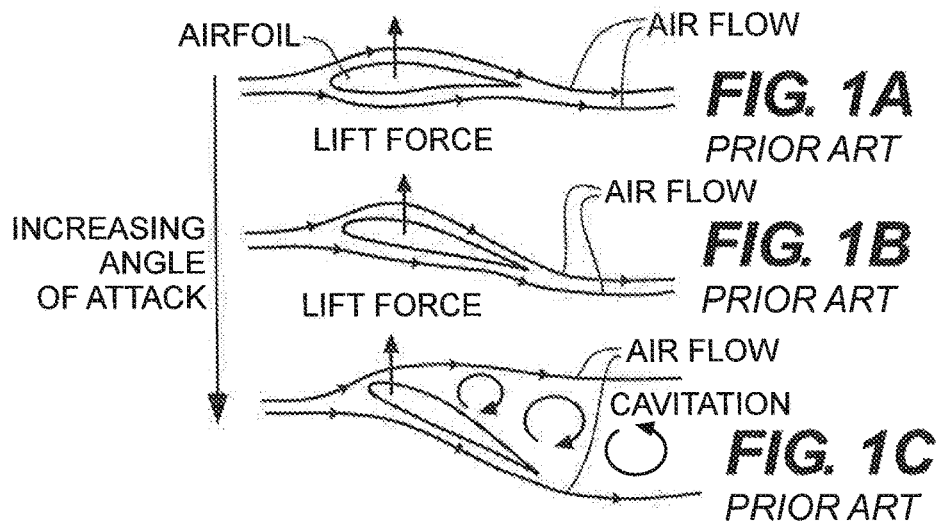
FIG. 1A PRIOR ART
FIG. 1B PRIOR ART
FIG. 1C PRIOR ART
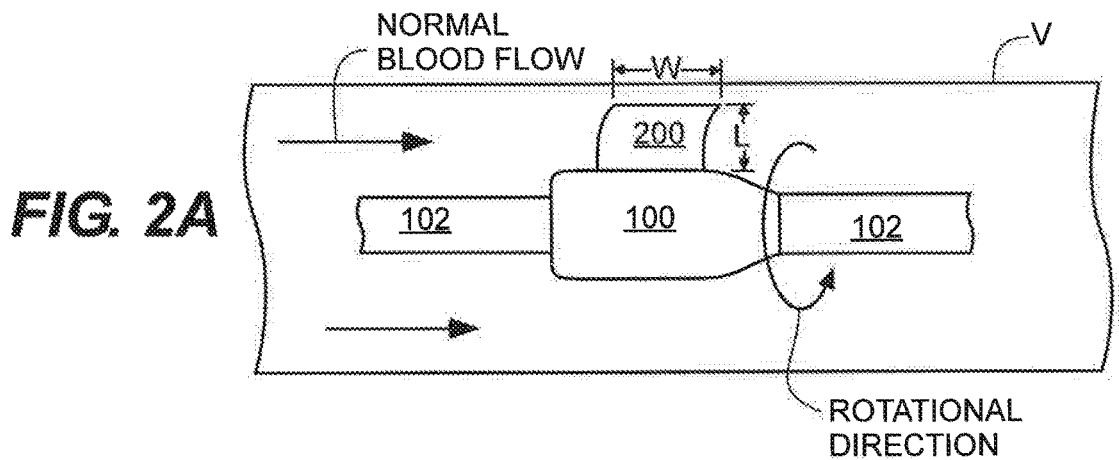
FIG. 2A
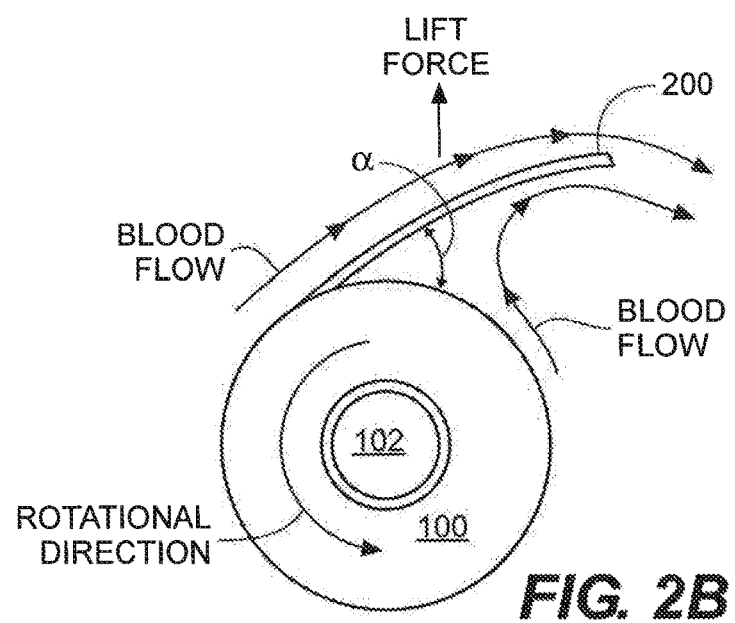
FIG. 2B

ROTATIONAL MEDICAL DEVICE WITH AIRFOIL

CROSS-REFERENCE TO RELATED APPLICATIONS

This application claims the benefit of U.S. Provisional Application Ser. No. 62/364,037, filed Jul. 19, 2016 and entitled BERNOULLI-EFFECT CROWN FOR ROTATIONAL DEVICES, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for removing tissue from body passageways, such as removal of atherosclerotic plaque from arteries, utilizing a rotational atherectomy device. In particular, the invention relates to a crown formed to create a Bernoulli-effect during rotation of the drive shaft to which the crown is attached.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®. The handle of the Rotablator® device includes a variety of components, including a compressed gas driven turbine, a mechanism for clamping a guide wire extending through the drive shaft, portions of a fiber optic tachometer, and a pump for pumping saline through the drive shaft.

The connection between the drive shaft (with its associated burr) and the turbine in the Rotablator® device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameter is sometimes referred to as a "step up technique" and is recommended by the manufacturer of the Rotablator® device. In the multiple burr technique it is necessary to use a new Rotablator® device for each such successive size burr. Accordingly, there is a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design. Preferably, the system provides an abrasive element that is capable of tracing a working diameter within the blood vessel that is larger than the resting diameter of the abrasive element. The present invention addresses at least these issues.

BRIEF DESCRIPTION OF THE SEVERAL VIEWS OF THE DRAWINGS

FIGS. 1A-1C provide schematic views of a prior art device.

FIG. 2A illustrates a side view of one embodiment of the present invention.

FIG. 2B illustrates a cutaway end front view of one embodiment of the present invention.

DETAILED DESCRIPTION OF THE INVENTION

Figure 3A:
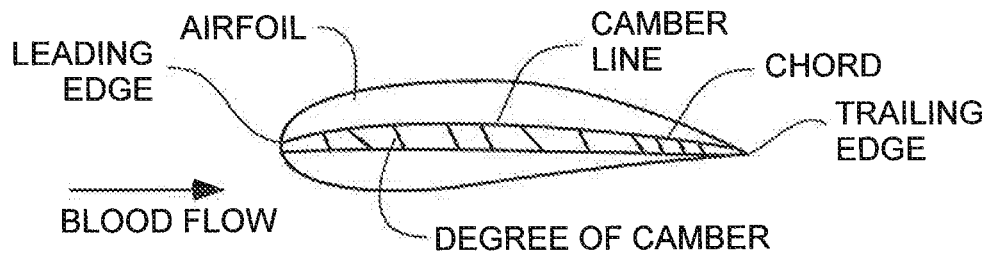
FIGS. 3A-3C illustrate various airfoil embodiments of the present invention.

Airfoils in the context of aircraft wings are well known and generally describe the concept of "lift" as the airfoil moves through the air fluid. As will be discussed below, the generally forward movement of an aircraft's airfoil through a fluid (air) may be modified to a rotational movement through a bodily fluid such as blood within a conduit such as an artery.

The inventions described below describe a structure that produces lift forces using an abrasive element comprising an airfoil moving through a fluid and that may be partially covered with an abrasive and attached to a rotational drive shaft capable of rotating the abrasive element comprising an airfoil at high speed within a fluid-filled bodily conduit such as an artery. The lift forces produced are generally directed in a radially outward direction away from the rotational axis of the drive shaft and tend therefore to pull the rotating abrasive element comprising an airfoil radially away from the rotational axis of the drive shaft. This, in turn, results in the rotating airfoil having a working trace and diameter that is larger than its resting diameter. The resting diameter of the abrasive element comprising an airfoil may made smaller than previously possible as a result of the increased working diameter during rotation, thereby increasing ease and comfort, while reducing possible trauma, in the movement of the drive shaft with the abrasive element attached thereto through the tortuous vasculature of the patient.

As with an aircraft wing or airfoil, several physical principles are involved in producing lift in the context of the rotational abrasive element comprising an airfoil.

An aircraft wing (airfoil) set at an effective angle of attack is very effective at changing the speed of the fluid flowing around the airfoil. The air above the airfoil experiences an increase in speed relative to the corresponding air below.

Bernoulli's principle generally asserts that a given parcel of air has high velocity when it has low pressure, and vice versa and may be best viewed as a consequence of Newton's laws.

As a partial consequence of the speed differential around the airfoil discussed above, the air pressure above the airfoil is below atmospheric pressure and the air pressure below the airfoil is above atmospheric pressure. And, the below-atmospheric pressure above the airfoil is much more pronounced than above-atmospheric pressure below the airfoil.

It is noteworthy that an aircraft airfoil does not have to be curved on top and/or flat on the bottom in order to work. A rounded leading edge can be helpful in creating the required air flows above and below the airfoil, but even a basically flat door will fly given the right speed and angle of attack.

Air passing above and below the airfoil does not do so in equal time. When lift is being produced, every air parcel passing above the airfoil arrives substantially early (compared to corresponding parcel below the wing) even though it has a longer path.

Most of the air above the wing arrives early in absolute terms (compared to undisturbed air), but this is not important, and the exceptions are doubly unimportant.

The variable contributing to the amount of lift produced by an airfoil include: circulation, speed of the airfoil, density of the airfoil, and the span of the wing of the airfoil (i.e., the longitudinal length of the airfoil of the abrasive element).

Generally, the coefficient of lift is proportional to the angle of attack and the circulation is proportional to the coefficient of lift times the airspeed.

These principles apply equally to a rotating abrasive element with an airfoil that is rotating within a fluid such as blood and may be used to modify the general abrasive structure comprising an airfoil to produce varying lift force results, each of these modifications is within the scope of the present invention.

The described rotation of the abrasive element comprising an airfoil through the surrounding fluid produces a modified fluid circulation in proportion to its angle of attack (and its rotational speed), both above and below the airfoil. This circulation, and in combination with the direction of rotation, means the fluid (blood) above the rotating airfoil is moving faster than the fluid below the rotating airfoil. This in turn produces low pressure at and above the rotating airfoil surface in accordance with Bernoulli's principle. The low pressure creates an upward force on the airfoil and pulls down on the fluid (blood) in accordance with all of Newton's laws.

Each of the following describes in different ways the lift process occurring during movement of the airfoil through the liquid:

1. The airfoil produces lift on the abrasive element comprising the airfoil because it is rotating through the fluid with at least one angle of attack.

2. The airfoil produces lift on the abrasive element comprising the airfoil because of the induced circulation of fluid around the airfoil during rotational movement through the fluid.

3. The airfoil produces lift on the abrasive element comprising the airfoil that is explained both by Bernoulli's principle and Newton's law of action and reaction.

FIGS. 1A-1C illustrate a known airfoil at varying (increasing) angles of attack which, in turn, provide increasing lift forces. The angle of attack is the angle of the airfoil relative to the incoming fluid. Thus, the angle of attack in FIG. 1A is essentially close to zero, but the shaping of the airfoil provides the necessary air flow, and resulting pressure differentials, necessary to achieve lift. FIG. 1B illustrates the concept of tilting the airflow at an angle to achieve greater air curving or air flowing around the airfoil as well as a the trailing edge of the airfoil to achieve increasing lift over the angle of attack of FIG. 1A. FIG. 1C shows an increased angle of attack over that of FIG. 1B, but with a smaller lift force because a stall condition, or near stall condition, is present. Note that in FIGS. 1A and 1B, the air flow that is turned over the upper and lower surfaces of the airfoil converge and reconnect. This condition is required to maintain lift and is not present in FIG. 1C as the upper air flow is not turned downward over the upper surface of the airfoil and does not converge with the lower airflow which is also turned downward. As a result, the lift, if any, in FIG. 1C is much lower than that of FIG. 1B.

The Figures generally illustrate in certain embodiments an abrasive element comprising an airfoil structure for providing a lift, or an outwardly radial force, relative to the nominal and/or rotational axis of the rotational drive shaft to which the abrasive element comprising an airfoil is connected or attached. The abrasive element comprising an airfoil is positioned near an exemplary occlusion, or other object of interest, and rotated via the rotational drive shaft that is driven in turn by an externally located prime mover such as an electric motor or turbine as is well known in the art. A general abrasive element 100 attached to a rotational drive shaft 102 with an airfoil 200 extending generally away from the direction of rotation of the abrasive element within an exemplary blood vessel V is shown in FIGS. 2A and 2B with angle of attack a and the resulting lift force generally directed radially outwardly from the nominal and rotational axis of the drive shaft 102 during high-speed rotation. The flow lines and accompanying arrows on the top and lower surfaces of the airfoil 200 show the curvature or turning of the fluid flow by both the upper and lower surfaces of the airfoil 200 to provide the requisite lift. Note that the lift force magnitude may be modified by changing a number of factors such as the rotational speed of the drive shaft 102 and, therefore, that of the airfoil, the length L and width W (surface area) of the airfoil 200, the curvature or camber of the airfoil 200, and the angle of attack a which is in certain embodiments dictated by the angle of connection between the abrasive element 100 and the airfoil 200. In some embodiments, the angle of attack a may be fixed and not variable while in other embodiments, the angle of attack a may become smaller as the rotational speed increases. Further, the curvature or camber of airfoil 200 may be fixed irrespective of rotational speed or may be variable, i.e., the curvature or camber of airfoil 200 may increase as rotational speeds increase. Thus, the airfoil 200 may comprise a fixation or variability of the angle of attack a in combination with a fixed or variable curvature or camber of airfoil 200. As discussed above, depending on the selected angle of attack a, the airfoil 200 may comprise no curvature or camber and may therefore be substantially flat.

Generally speaking, the most important variable in creating lift with an airfoil is the angle of attack. To a lesser extent is the amount of curvature or camber in the airfoil. Thus, FIGS. 3A-3 illustrate potential airfoil shapes that may be used to generate lift as discussed herein.

Figure 3B:
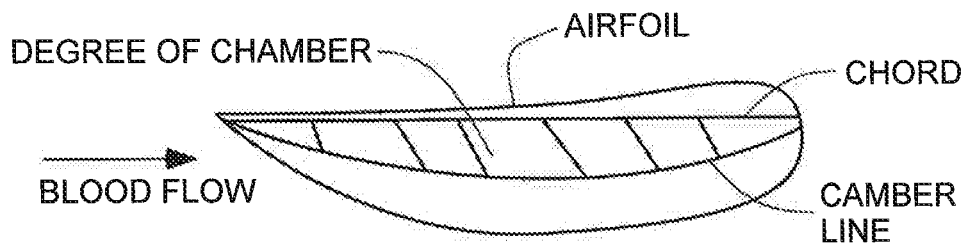

FIG. 3A illustrates the degree of camber relative to a chord drawn from the leading edge to the trailing edge of the exemplary airfoil. The area between the chord and the camber line is the degree of camber, wherein the chord is the line connecting the leading edge with the trailing edge and the camber line is the line running from the leading edge and following the curvature of the airfoil. FIG. 3B illustrates essentially the reverse of FIG. 3B which, at the appropriate angle of attack will result in generation of a lift force. FIG. 3B is representative, for example, of an aircraft flying upside down, with lift forces made possible by modifying the angle of attack of the wings.

Figure 3C:
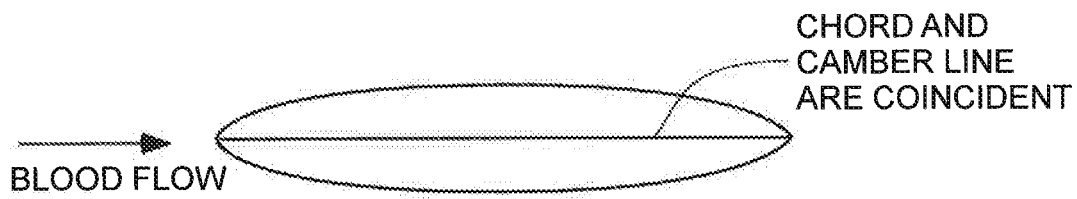

Finally, FIG. 3C provides a symmetric airfoil, wherein the chord and the camber line are coincident. As with the previous exemplary airfoils, the airfoil of FIG. 3C will generate lift forces with the appropriate angle(s) of attack. Any variation of the embodiments of FIGS. 3A-3C is within the scope of the various airfoil design embodiments of the present invention.

Figure 4:
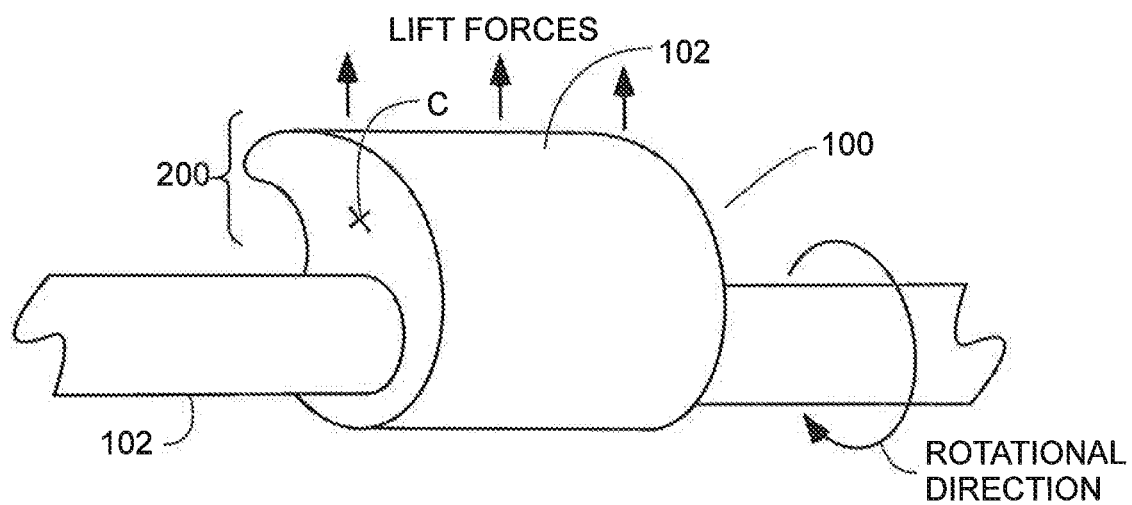
FIG. 4 is a broken away, perspective view of one embodiment of the present invention.
Figure 5:
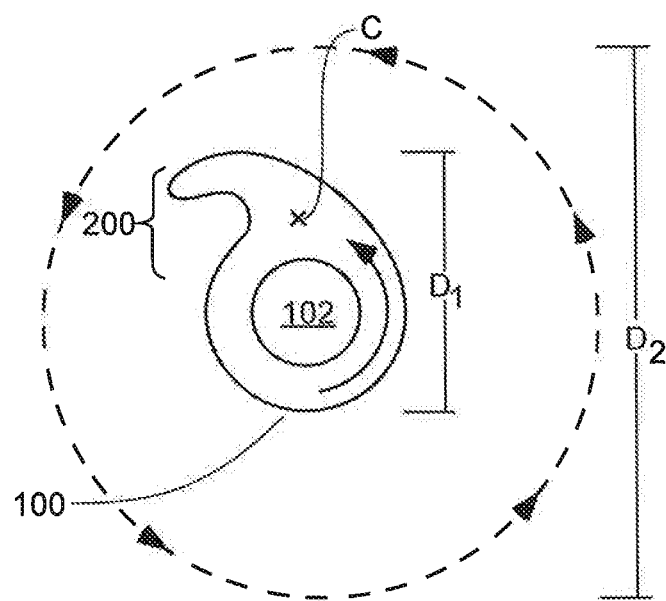
FIG. 5 is a cross-section view of one embodiment of the present invention.

A particular embodiment of an abrasive element 100 with airfoil 200 and in operative connection or attachment with a rotational drive shaft 102 is shown in FIG. 4. In this embodiment, the airfoil 200 is formed as an integration of the abrasive element 100 and attached to the drive shaft 102 as an integrated element. The airfoil 200 comprises a curvature or camber as shown which may, or may not be, fixed as discussed above. Lift forces resulting from the curved fluid flow over and under the rotating airfoil 200 are illustrated as arrows generally leading away from the rotational axis or nominal axis of the drive shaft 102. As shown in FIG. 5, during high-speed rotation of the drive shaft 102 of FIG. 4, the working diameter $D_2$ increases, at least in part due to the produced lift forces, to a diameter that is greater than the resting diameter $D_1$ as illustrated by the arrows tracing the orbital working path of abrasive element 100.

FIGS. 4 and 5 further illustrate the radial offset of the center of mass C in abrasive element 100 which will further work in combination with the airfoil 200 to create a larger working diameter than resting diameter when the center of mass C is generally offset in the direction of the generated lift forces.

As discussed above, the rotational device as illustrated comprises an abrasive structure or element such as an abrasive element or structure such as a crown and/or an abrasive band or ring attached to a drive shaft having an axis of rotation. Generally in these embodiments, the airfoil is either formed integrally with the abrasive structure or element or is operatively attached thereto.

Figure 6A:
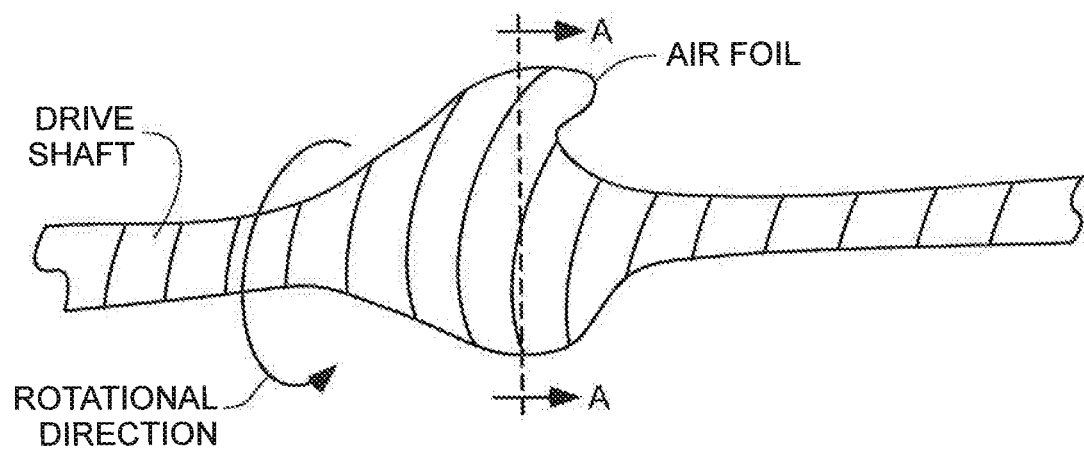
FIG. 6A is a broken away perspective view of one embodiment of the present invention.
Figure 6B:
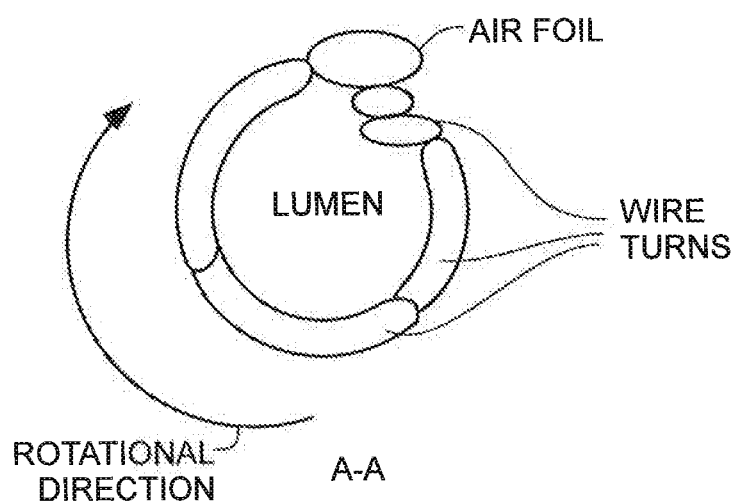
FIG. 6B is a cross-section view of the embodiment of FIG. 6A.

Alternatively, as also discussed above and as shown in FIGS. 6A and 6B, the abrasive element may comprise an enlarged section of the drive shaft comprising an abrasive section of the drive shaft with an airfoil formed therein or thereon. FIG. 6A thus illustrates an enlarged drive shaft with an airfoil formed in and by the wire turns of the drive shaft itself. FIG. 6B shows the enlarged drive shaft in cross section at the airfoil formation. FIGS. 6A and 6B illustrate a concentric enlarged drive shaft, except for the extending airfoil, and that is symmetric about a longitudinal axis therethrough.

Figure 6C:
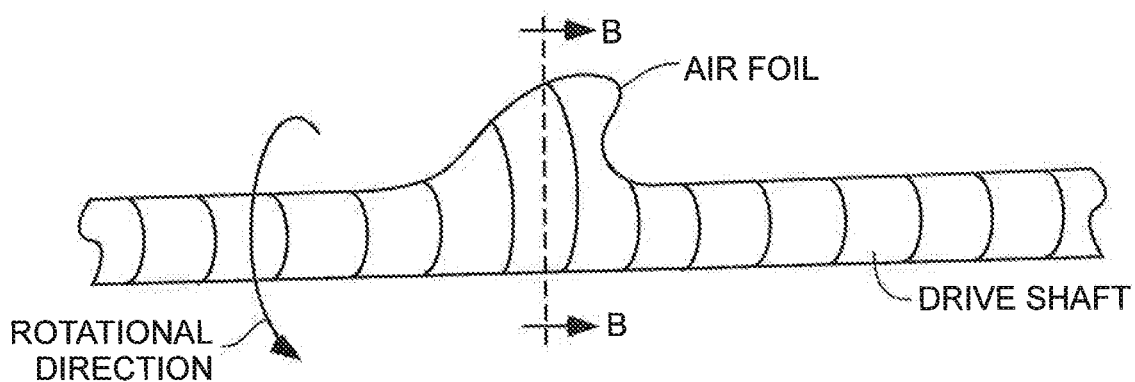
FIG. 6C is a broken away perspective view of one embodiment of the present invention.
Figure 6D:
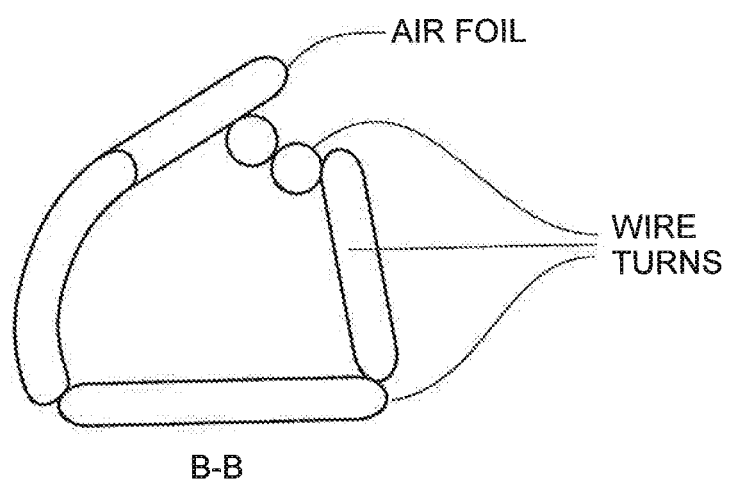
FIG. 6D is a cross-section view of the embodiment of FIG. 6C

FIGS. 6C and 6D illustrate an eccentric enlarged drive shaft that is asymmetric about a longitudinal axis therethrough with the airfoil formed in and by the wire turns of the drive shaft.

Other embodiments may comprise an enlarged section of the drive shaft in combination with an airfoil structure operatively connected or attached thereto. Generally in these embodiments, at least a portion of the enlarged section of the drive shaft may be coated with abrasive material as is well known to the skilled artisan.

Figure 7A:
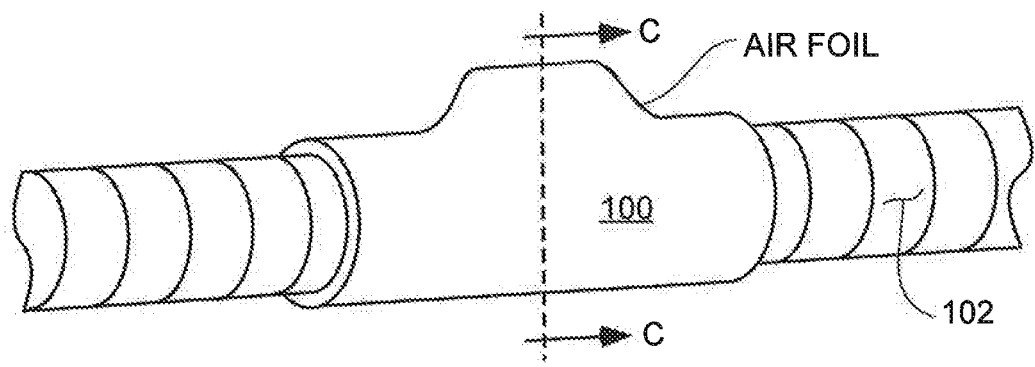
FIG. 7A is a broken away perspective view of one embodiment of the present invention.
Figure 7B:
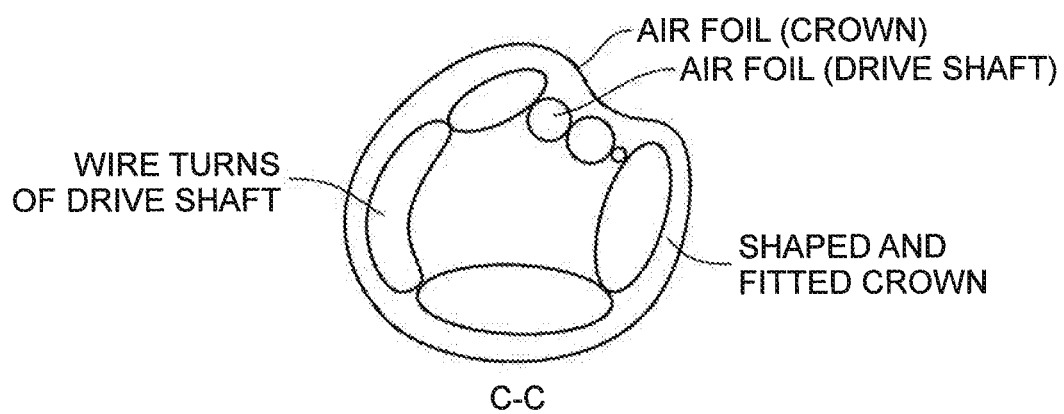
FIG. 7B is a cross-section view of the embodiment of FIG. 7A.

Alternatively, an abrasive crown may be fitted over the enlarged section of the drive shaft and operatively attached thereto. As shown in FIGS. 7A and 7B, when fitted over the enlarged section of the drive shaft and operatively attached thereto, the abrasive crown may be spaced proximally away from a distal end of the drive shaft such that a portion of the drive shaft extends distally beyond the abrasive crown. The fitted abrasive crown may be shaped to complement the outer shaping of the enlarged drive shaft with the airfoil formed thereon or therein as shown in FIGS. 7A-7B so that the fitted abrasive crown comprises a complementary shaping that matches and aligns with the airfoil formed within the enlarged section of the drive shaft.

Figure 8:
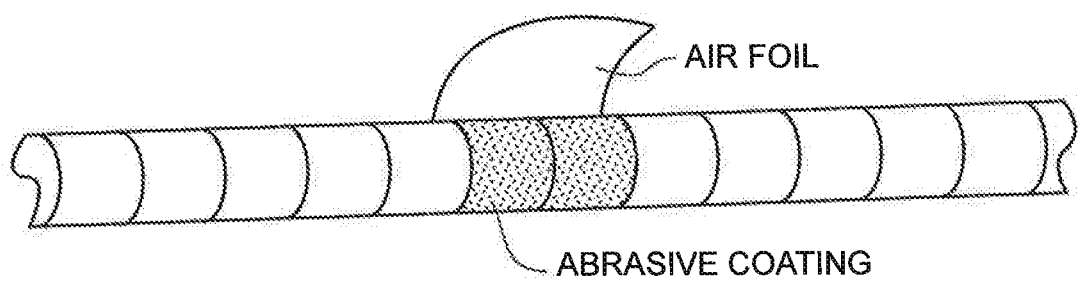
FIG. 8 is a broken away perspective view of one embodiment of the present invention.

Still more alternatively, a drive shaft having otherwise substantially continuously the same diameter may comprise an airfoil formed by the wire turns of the drive shaft at least partially within the abrasive section of the drive shaft as is done in the embodiments illustrated in FIGS. 6A-6D, except without requirement or aid of the enlarging of the drive shaft. Still further, a drive shaft may comprise a generally constant diameter but with an abrasive section comprising an abrasive coating and an airfoil operatively connected thereon or thereto as in FIG. 8. In these cases, the enlarged working diameter is drawn primarily from the lift forces that are generated by the airfoil and to a lesser extent the slight mass offset from the nominal or rotational axis of the drive shaft.

Figure 9:
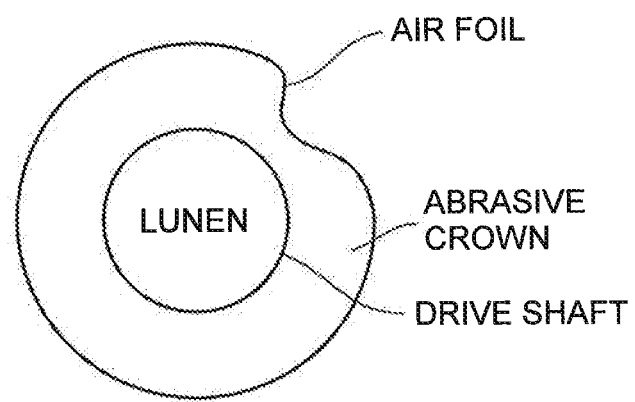
FIG. 9 is a cross-section view of one embodiment of the present invention.

Another embodiment may comprise a fitted abrasive crown having an airfoil structure to achieve the lift function, either integrally formed with the fitted abrasive crown or operatively attached or connected thereto as generally shown in FIG. 2A. In this case, when formed integrally, the airfoil 200 may be formed by grinding down or cutting the abrasive crown. See this in cross-sectional view in FIG. 9.

The enlarged section of the drive shaft in the above embodiments may be symmetric about the longitudinal and/or vertical axes or it may be asymmetric. The center of mass of the enlarged section of the drive shaft may further be located on the nominal or rotational axis of the drive shaft or may be radially offset from the nominal or rotational axis of the drive shaft to assist in achieving an orbital motion, i.e., the working diameter is greater than the resting diameter, during high-speed rotation in combination with the lift forces produced. Similarly, the fitted abrasive crown may be symmetric or asymmetric with a center of mass that may be generally located on the nominal or rotational axis of the drive shaft or may be radially offset therefrom.

Similarly, the center of mass of the embodiments comprising an abrasive element attached to a non-enlarged drive shaft may be located on the nominal or rotational axis of the drive shaft or may be radially offset therefrom and, in either case, the abrasive element in this embodiment may comprise a symmetric shape or an asymmetric shape as the mass may be distributed accordingly within the abrasive element as needed or desired during manufacture through the use of mass distribution techniques such as geometric eccentricity (asymmetry about a longitudinal axis), use of materials having varying densities, and use of voids or holes or spaces therein.

Additional abrasive structures or elements for use with rotational devices will occur to the skilled artisan, each of these additional structures are within the scope of the present invention.

No matter the form or type of abrasive structure (including abrasive crowns, burrs, enlarged sections of the drive shaft, straight sections (non-enlarged) of the drive shaft, etc.) each of the various embodiments of the abrasive structure share one commonality; that is, an airfoil structure extending outwardly and generally radially away from the abrasive structure itself and from the rotational axis of the drive shaft.

Generally as shown the outer surface is smoothly radiused, with a concave radiused region shown formed on the bottom of the lip.

Generally, the "lift" created by the wing-like profile of the airfoil of the rotating abrasive structure will work to move the rotating abrasive element or structure off of the rotational axis of the drive shaft, i.e., orbital motion will be achieved, so that a working diameter of the rotating abrasive structure or element will be larger or greater than its resting diameter. In addition, certain embodiments may comprise a center of mass that is located radially, and in some cases also laterally, off of the drive shaft's rotational axis.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 6,295,712, "ROTATIONAL ATHERECTOMY DEVICE";

U.S. Pat. No. 6,494,890, "ECCENTRIC ROTATIONAL ATHERECTOMY DEVICE";

U.S. Pat. No. 6,132,444, "ECCENTRIC DRIVE SHAFT FOR ATHERECTOMY DEVICE AND METHOD FOR MANUFACTURE";

U.S. Pat. No. 6,638,288, "ECCENTRIC DRIVE SHAFT FOR ATHERECTOMY DEVICE AND METHOD FOR MANUFACTURE";

U.S. Pat. No. 5,314,438, "ABRASIVE DRIVE SHAFT DEVICE FOR ROTATIONAL ATHERECTOMY";

U.S. Pat. No. 6,217,595, "ROTATIONAL ATHERECTOMY DEVICE";

U.S. Pat. No. 5,554,163, "ATHERECTOMY DEVICE";

U.S. Pat. No. 7,507,245, "ROTATIONAL ANGIOPLASTY DEVICE WITH ABRASIVE CROWN";

U.S. Pat. No. 6,129,734, "ROTATIONAL ATHERECTOMY DEVICE WITH RADIALLY EXPANDABLE PRIME MOVER COUPLING";

U.S. patent application Ser. No. 11/761,128, "ECCENTRIC ABRADING HEAD FOR HIGH-SPEED ROTATIONAL ATHERECTOMY DEVICES";

U.S. patent application Ser. No. 11/767,725, "SYSTEM, APPARATUS AND METHOD FOR OPENING AN OCCLUDED LESION";

U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE";

U.S. patent application Ser. No. 12/388,703, "ROTATIONAL ATHERECTOMY SEGMENTED ABRADING HEAD AND METHOD TO IMPROVE ABRADING EFFICIENCY"; and U.S. patent application Ser. No. 13/624,313, "ROTATIONAL ATHERECTOMY DEVICE WITH ELECTRIC MOTOR".

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A rotational atherectomy system having a prime mover, a rotational drive shaft in operative connection with the prime mover, the system further comprising an abrasive element in operative attachment with the rotational drive shaft and spaced proximally away from a distal end of the drive shaft such that a portion of the drive shaft extends distally beyond the abrasive element, and an airfoil in operative connection with the abrasive element.

2. The rotational atherectomy system of claim 1, wherein the rotational drive shaft comprises an enlarged drive shaft section wherein the abrasive element is in operative attachment with the enlarged drive shaft section.

3. The rotational atherectomy system of claim 1, wherein the airfoil comprises an upper surface and a lower surface, a leading edge and a trailing edge, wherein the leading edge is in operative connection with the abrasive element and wherein the airfoil comprises a curved upper surface.

4. The rotational atherectomy system of claim 3, further comprising the airfoil having a camber line that is not coincident with a chord drawn between the leading edge and the trailing edge.

5. The rotational atherectomy system of claim 1, further comprising the abrasive element comprising a resting diameter and a working diameter achieved during high-speed rotation, wherein the working diameter is greater than the resting diameter.

6. A rotational atherectomy system comprising a prime mover, a rotational drive shaft formed of wire turns and in operative connection with the prime mover, and further comprising an abrasive section located on the rotational drive shaft and spaced proximally away from a distal end of the drive shaft such that a portion of the drive shaft extends distally beyond the abrasive section, and an airfoil at least partially connected with the abrasive section.

7. A method for increasing the working diameter of an abrasive element that is in operative connection with a rotational drive shaft and prime mover, wherein the abrasive element is spaced proximally away from a distal end of the drive shaft such that a portion of the drive shaft extends distally beyond the abrasive element, and wherein an airfoil is in operative connection with the abrasive element, the method comprising:

rotating the drive shaft and abrasive element in the direction of a leading edge of the airfoil;

generating lift forces with the airfoil during the rotating; and thereby causing the rotating abrasive element to begin tracing a working path that comprises a diameter that is greater than [a] resting diameter of the abrasive element.

8. The method of claim 7, wherein the abrasive element comprises an abrasive crown, wherein the airfoil is in operative connection to the abrasive crown via a first portion of the airfoil and wherein at least a second portion of the airfoil is integrally formed with the abrasive crown.

* * * * *